US00PP17817P3

(12) United States Plant Patent
Andersen

(10) Patent No.: US PP17,817 P3
(45) Date of Patent: Jun. 19, 2007

(54) ***SCHLUMBERGERA* PLANT NAMED 'THOR-LIVIA'**

(50) Latin Name: *Schlumbergera truncata*
Varietal Denomination: THOR-LIVIA

(75) Inventor: Jørgen Kurt Andersen, Odense SÖ (DK)

(73) Assignee: Gartneriet Thoruplund A/S, Odense SO (DK)

( * ) Notice: Subject to any disclaimer, the term of this patent is extended or adjusted under 35 U.S.C. 154(b) by 0 days.

(21) Appl. No.: 11/335,745

(22) Filed: Jan. 20, 2006

(65) Prior Publication Data

US 2006/0206975 P1 Sep. 14, 2006

(30) Foreign Application Priority Data

Jan. 20, 2005 (EM) ..... 2005/0091

(51) Int. Cl.
*A01H 5/00* (2006.01)

(52) U.S. Cl. ..... Plt./372

(58) Field of Classification Search ..... Plt./372
See application file for complete search history.

*Primary Examiner*—Kent Bell
*Assistant Examiner*—Annette H Para
(74) *Attorney, Agent, or Firm*—Foley & Lardner, LLP

(57) ABSTRACT

A new and distinct *Schlumbergera* plant named 'THOR-LIVIA' particularly characterized by large upright to vertical flowers; freely flowering white, light purple and red-purple colored flowers; large quantity of flowers per plant; and slow growth rate and freely branching growth habit.

4 Drawing Sheets

Latin name of the genus and species of the plant claimed: *Schlumbergera truncata.*
Variety denomination: 'THOR-LIVIA'.

BACKGROUND OF THE INVENTION

The present invention relates to a new and distinct cultivar of *Schlumbergera* plant, botanically known as *Schlumbergera truncata,* and hereinafter referred to by the cultivar name 'THOR-LIVIA'.

*Schlumbergera* (formerly *Zygocacatus*) of the Cactaceae family, consists of 6 known species which are epiphytic cacti and native to Brazil. Common names for *Schlumbergera* plants include: Crab Cactus for the cultivar's claw-like phylloclade margin, Thanksgiving Cactus for cultivars which bloom in November, and Christmas Cactus for cultivars which bloom in December.

The new *Schlumbergera* cultivar is a product of a controlled breeding program conducted by the inventor, Jørgen Kurt ANDERSEN, in Fyn, Denmark. The objective of the breeding program was to develop a new *Schlumbergera* cultivar with upright plant habit, freely branching habit and large flowers with a unique color combination.

The new *Schlumbergera* cultivar originated from an outcrossing made by the inventor, Jørgen Kurt ANDERSEN, in 2001 in Fyn, Denmark. The female or seed parent is an unnamed, unpatented *Schlumbergera truncata* cultivar. The male or pollen parent is an unnamed, unpatented *Schlumbergera truncata* cultivar. The new *Schlumbergera* cultivar was discovered and selected by the inventor as a single flowering plant within the progeny of the stated outcrossing in a controlled environment in 2002 in Fyn, Denmark, on the basis of its flower color and freely branching habit.

Asexual reproduction of the new *Schlumbergera* cultivar by phylloclade cuttings taken and propagated, and followed by trial production batches, was first performed on 25$^{th}$ November 2001 in Fyn, Denmark, and has demonstrated that the combination of characteristics as herein disclosed for the new cultivar are firmly fixed and retained through successive generations of asexual reproduction. The new cultivar reproduces true to type.

BRIEF DESCRIPTION OF THE INVENTION

The following traits have been repeatedly observed and are determined to be unique characteristics of 'THOR-LIVIA' which in combination distinguish this *Schlumbergera* as a new and distinct cultivar:

1. Large upright to vertical flowers;
2. Freely flowering white, light purple and light red-purple colored flowers;
3. Large quantity of flowers per plant; and
4. Slow growth rate and freely branching growth habit.

Plants of the new *Schlumbergera* cultivar 'THOR-LIVIA' differ from plants of the parental cultivars in the following characteristics:

1. Many shoote and flowers

Of the many commercial cultivars known to the present inventor, the most similar in comparison to the new *Schlumbergera* cultivar 'THOR-LIVIA' is the *Schlumbergera* cultivar 'THOR-BRITTA' (unpatented) in the following characteristics:

1. Plants of the new *Schlumbergera* cultivar 'THOR-LIVIA' have more lateral branches (about 14 when 3 phylloclade cuttings planted per plant) than plants of the cultivar 'THOR-BRITTA' (about 9 when 3 phylloclade cuttings planted per plant).
2. Plants of the new *Schlumbergera* cultivar 'THOR-LIVIA' have thicker and lighter green phylloclades (about 6 mm; yellow-green, RHS 146A) than 'THOR-BRITTA' (about 4 mm; green, RHS 137A).

3. Plants of the new *Schlumbergera* cultivar 'THOR-LIVIA' are narrower and more compact (about 20 cm) than the plants of the cultivar 'THOR-BRITTA' (about 27 cm).
4. Plants of the new *Schlumbergera* cultivar 'THOR-LIVIA' have larger and more flowers (diameter about 5.5 cm and height about 7.5 cm; about 40 to 45 flowers) than the plants of the cultivar 'THOR-BRITTA' (diameter about 4.5 cm and height about 6.0 cm; about 30 to 35 flowers).

BRIEF DESCRIPTION OF THE PHOTOGRAPHS

The accompanying photographs illustrate the overall appearance of the new *Schlumbergera* cultivar 'THOR-LIVIA' showing the colors as true as is reasonably possible with colored reproductions of this type. Colors in the photographs may differ slightly from the color values cited in the detailed botanical description, which accurately describe the color of 'THOR-LIVIA'.

DETAILED BOTANICAL DESCRIPTION

Figure 1:
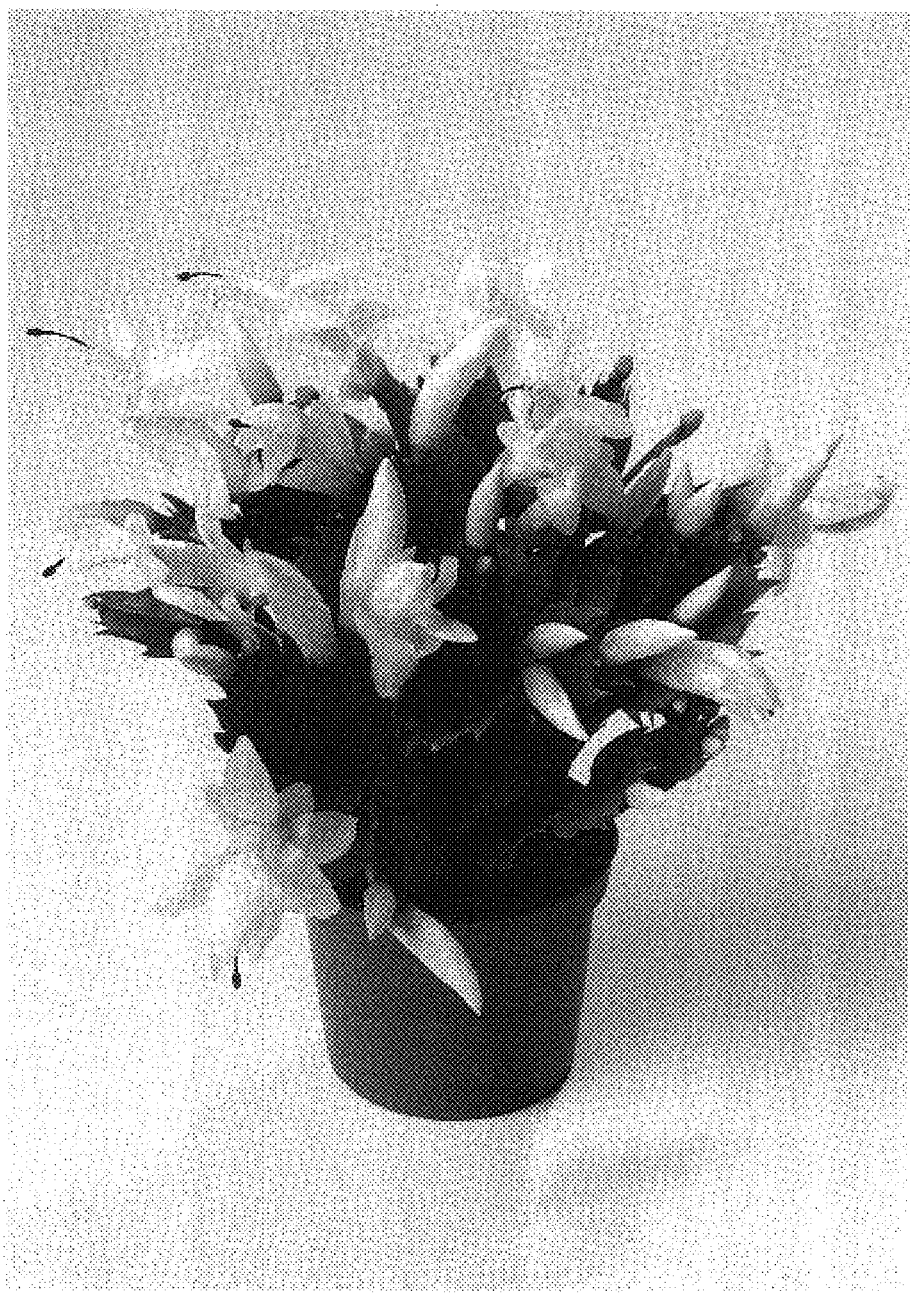
FIG. 1 shows a side perspective view of a typical flowering plant of 'THOR-LIVIA' grown in a 10.5 cm pot, at 10 months of age.
Figure 2:
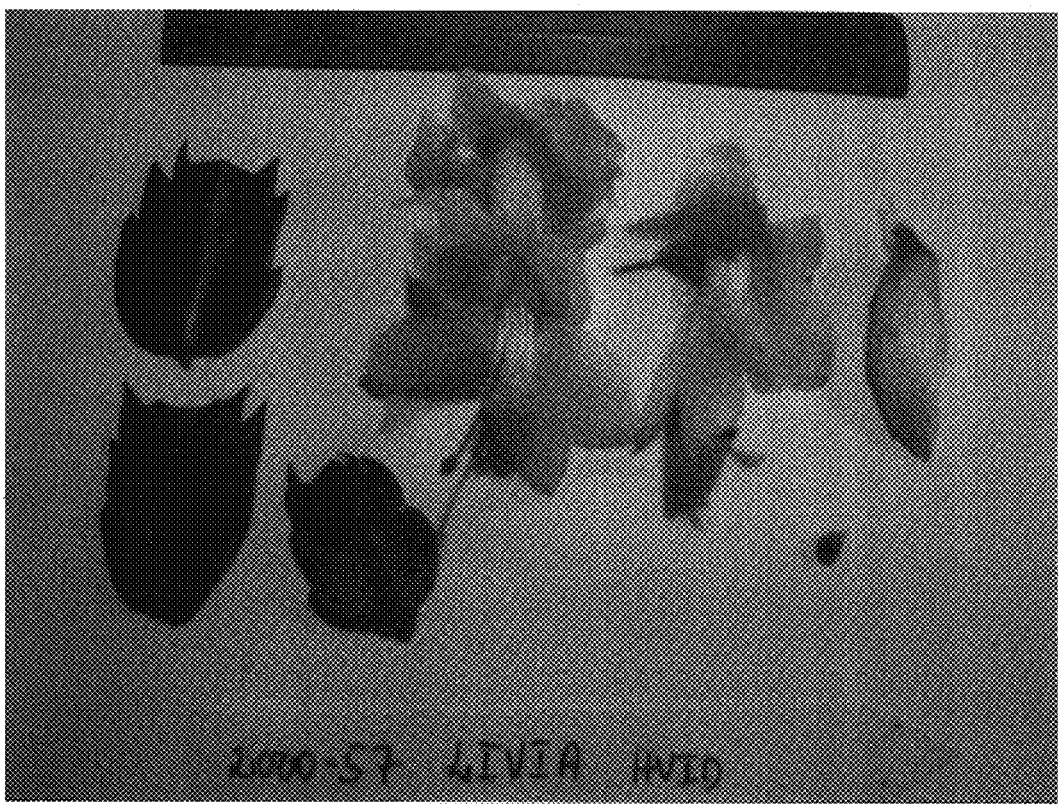
FIG. 2 shows a close-up view of immature and mature flowers and phylloclades of 'THOR-LIVIA'.
Figure 3:
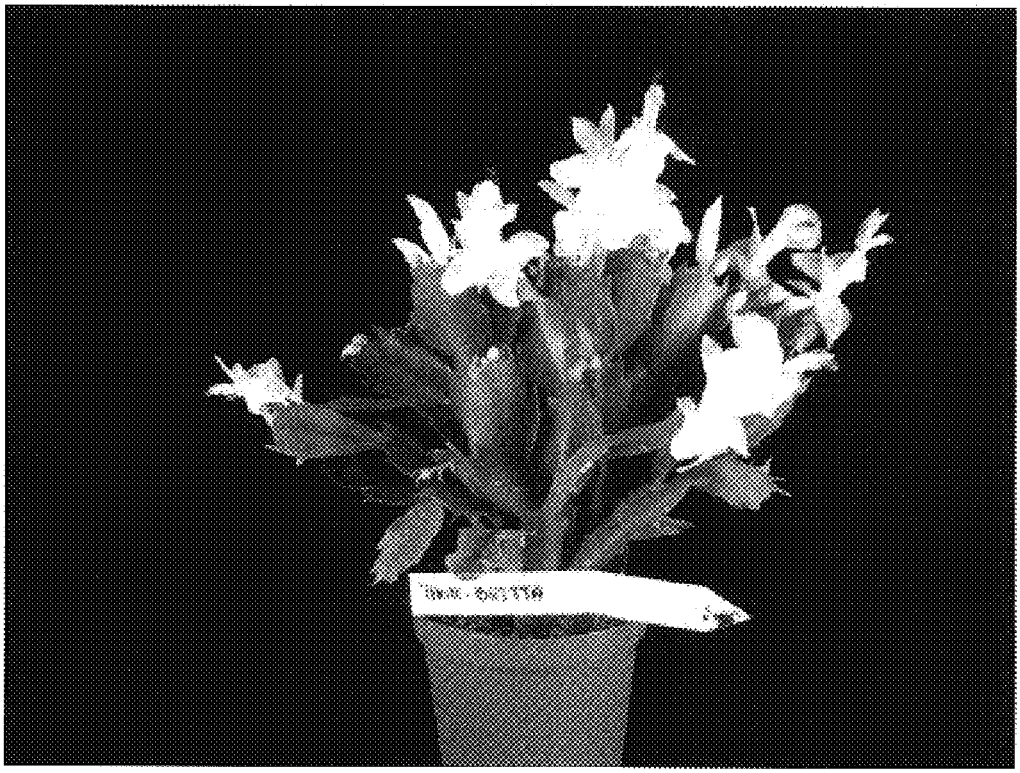
FIG. 3 shows a side perspective view of a typical flowering plant of 'THOR-BRITTA' grown in a 10.5 cm pot, at 10 months of age.
Figure 4:
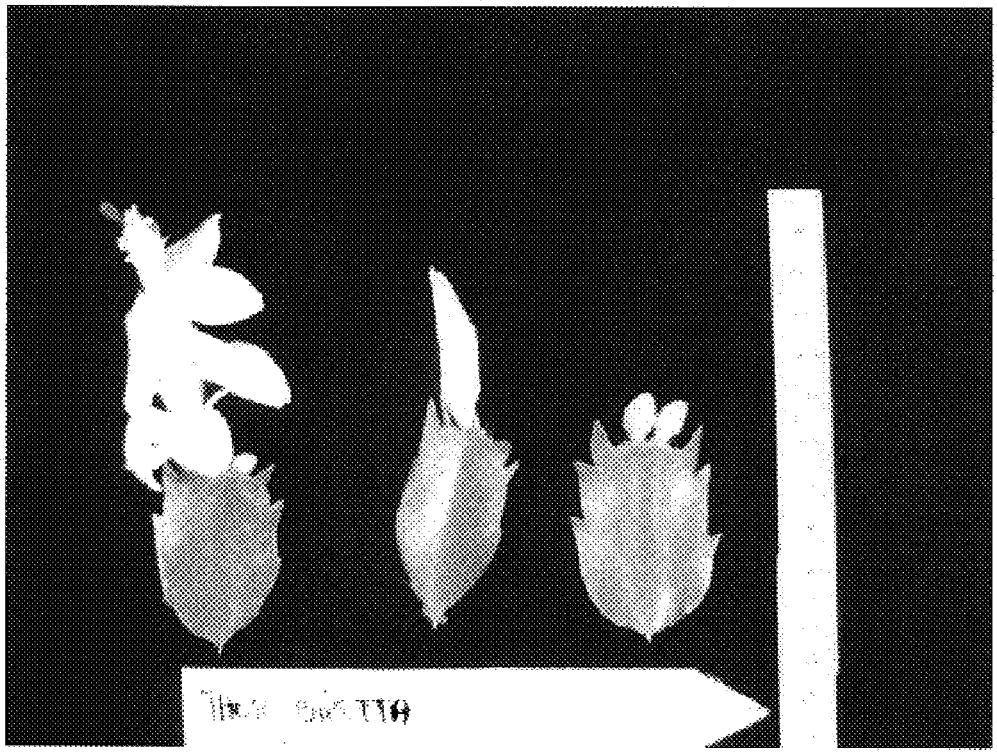
FIG. 4 shows a close-up view of flowers and phylloclades of 'THOR-BRITTA'.

The new *Schlumbergera* cultivar 'THOR-LIVIA' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'THOR-LIVIA' as grown in a glass-covered greenhouse in Fyn, Denmark, under conditions which closely approximate those generally used in commercial practice. Plants of 'THOR-LIVIA' are themo-photoperiodic and will develop buds and bloom best under short day conditions (less than 12 hours of sunlight for a period of 6 weeks) and cool night temperatures between 13° C. and 18° C. No growth retardants were used when growing plants of 'THOR-LIVIA'.

Color references are made to The Royal Horticultural Society Colour Chart (R.H.S.), $4^{th}$ edition, except where general colors of ordinary significance are used. The photographs and descriptions were taken during the Fall of 2005 in Fyn, Denmark, when outdoor day temperatures averaged 20° C. and outdoor night temperatures averaged 18° C. The age of the plants described is 20 weeks.

Classification:
- *Botanical.*—*Schlumbergera truncata.*
- *Common name.*—Thanksgiving Cactus.

Parentage:
- *Female or seed parent.*—Unnamed, unpatented *Schlumbergera truncata.*
- *Male or pollen parent.*—Unnamed, unpatented *Schlumbergera truncata.*

Propagation: By phylloclade cuttings.
- *Time and temperature to initiate roots.*—In a greenhouse, about 30 days at 18° C. to 21° C. 21° C.
- *Time and temperature to produce a rooted cutting.*—In a greenhouse, about 20 days at at 18° C. to 21° C.
- *Rooting habit and description.*—Fine, well-branched and RHS 155B white in color.

Plant:
- *Type.*—Perennial, Epiphyte.
- *Growth habit.*—Initially erect and upright, becoming pendent as lateral branches lengthen.
- *Branching habit.*—Freely branching, with three or more new phylloclades forming at the apex of older phylloclades.
- *Vigor.*—Slow growth rate.
- *Crop time.*—After rooting, about 10 months are required to produce a finished flowering plant in an 11 cm pot.
- *Size at maturity.*—Height (soil level to top of plant, including flowers): About 18 cm. Spread: About 20 cm.

Stem: None, older phylloclades may turn woody with age (several years).

Lateral branches:
- *Arrangement.*—Phylloclades form at the apex of older phylloclades to form branches.
- *Quantity.*—About 14, when 3 phylloclade cuttings planted per pot.
- *Length.*—Primary: About 4 cm (1 phylloclade). Secondary: About 8.5 cm (2–3 phylloclades).
- *Width.*—About 3.5 cm.
- *Aspect.*—Upright (from basal phylloclade).
- *Strength.*—Strong (from basal phylloclade).
- *Appearance.*—Shiny.
- *Pubescence.*—None.
- *Color.*—Green, RHS N138A.

Phylloclade:
- *Arrangement.*—Single and sequential.
- *Quantity per lateral branch.*—About 3.
- *Length.*—About 4 cm.
- *Width.*—About 3.5 cm.
- *Thickness.*—About 6 mm (center of phylloclade).
- *Overall shape.*—Oval, truncated.
- *Apex shape.*—Truncate with 2 protruding marginal teeth (about 8 to 9 mm in length), forming a claw-like shape.
- *Base shape.*—Rounded, obtuse.
- *Margin.*—Serrated; about 6 teeth (5–7 mm in length).
- *Texture.*—Glabrous, smooth.
- *Pubescence.*—None.
- *Color of upper surface.*—Immature: Yellow-green, RHS 146A. Mature: Yellow-green, RHS 147A. Margin: Yellow-green, RHS 146A.
- *Color of lower surface.*—Immature: Yellow-green, RHS 146B. Mature: Yellow-green, RHS 147B. Margin: Yellow-green, RHS 146A.
- *Venation.*—Pattern: Costate. Color: Upper surface: Yellow-green, RHS 146A. Lower surface: Yellow-green, RHS 147B.

Areole: Not true areole structure; tip of phylloclade is barbellate, 4–6 short hairs or bristles.

Inflorescence description:
- *Arrangement and appearance.*—Single, double or triple sessile flowers borne on apical end of phylloclades. Flowers are hose-in-hose and zygomorphic. When flowers are fully open, they form a right angle to the phylloclade. Flowers persistent; petals fold and wither slowly.

*Natural flowering season.*—Flowering occurs between October and December (northern hemisphere), but can be changed depending on short day photo-treatments.

*Flowering response time.*—About 8 to 9 weeks from planting.

*Rate of flowers opening.*—About 2 per week, depending on temperature and light.

*Flowering longevity* (*dependent on temperature and light conditions*).—About 5 to 6 days.

*Fragrance.*—None.

*Quantity of flowers per lateral branch.*—About 1 to 3.

*Quantity of buds per lateral branch.*—About 2.

*Quantity of flowers and buds per plant.*—About 40 to 45.

*Flower bud.*—Length: Ranging from 0 to 35 mm (before anthesis). Width: Ranging from 0 to 8 mm (before anthesis). Shape: Lanceolate. Color: Initially, Grey-orange, RHS 167A; Later, White, RHS N155C (base) and white, RHS 155B (apex).

*Flower.*—Type: Single. Shape: Tubular, hose-in-hose triple perianth. Aspect: Initially facing upward, later facing outward (right angle to phylloclade). Persistent or self-cleaning: Persistent, but drops after withering.

*Corolla size.*—Height: About 7.5 cm (including ovary). Diameter: About 5 to 6 cm. Tube length: About 5 cm. Tube diameter: About 9 mm.

*Petals.*—Quantity: Apical Whorl: About 8; Basal whorl: About 5 to 7. Length: About 2.8 cm Width: About 1.7 cm Shape: Oblong. Apex: Acute. Base: Apical Whorl: Fused; Basal Whorl: Free. Margin: Entire Appearance: Almost Translucent. Texture: Silky, smooth, glabrous (both surfaces). Color of Upper Surface (when opening): Petal Edges: Light red-purple, RHS 69D, translucent; Petal Center: Light red-purple, RHS 69B; Petal Margin: Light red-purple, RHS 69D; Tube: Light Purple, RHS 75D. Color of Lower Surface (when opening): Petal Edges: Light red-purple, RHS 69D, translucent; Petal Center: Light red-purple, RHS 69C; Petal Margin: Light red-purple, RHS 69D; Tube: White, RHS N155C. Color of Upper Surface (when fully opened): Petal Edges: White, RHS N155C; Petal Center: Light purple, RHS 75D; Petal Margin: White, RHS N155C; Tube: Light Purple, RHS 75D; "ring" at opening of tube, purple, RHS N74A. Color of Lower Surface (when fully opened): Petal Edges: Light red-purple, RHS 69D; Petal Center: White, RHS N155C; Petal Margin: Light red-purple, RHS 69D; Tube: White, RHS N155C.

*Petaloids.*—Quantity: About 7 to 9. Length: About 2.5 cm Width: About 1.2 cm Shape: Oblong. Apex: Acute. Base: Fused. Margin: Entire. Texture (both surfaces): Silky. Color (mature and immature): Light red-purple, RHS 69D.

*Sepals.*—Quantity: About 5. Length: About 1.0 cm. Width: About 1.0 cm. Shape: Ovate. Apex: Obtuse to rounded. Base: Truncate. Margin: Entire. Texture (both surfaces): Glabrous. Color (Immature and Mature): Upper surface: Light red-purple, RHS 69D; margin: Red-purple, RHS 69C. Lower surface: Light red-purple, RHS 69D; margin: Red-purple, RHS 69C.

Reproductive organs:

*Androecium.*—Stamen: Quantity: Many (about 30 to 40), polyandrous, phaneranherous (Obviously protruding), incurved. Some filaments fused to perianth tube (connate). Length: About 45 mm. Color: White, RHS 155D. Anther: Shape: Basifixed, ovoid. Length: About 1 mm. Color: Light yellow, RHS 11D. Filament: Length: About 40 to 45 mm. Color: White, RHS 155D, translucent. Pollen: Amount: Abundant. Color: Light yellow, RHS 11D.

*Gynoecium.*—Pistil: Quantity: 1. Shape: Slightly curved. Length: About 55 mm. Stigma: Shape: Initially ovoid, opening to claw-like shape. Color: Red-purple, RHS N74A. Style: Length: About 45 mm. Color: Red-purple, RHS N74A. Ovary: Shape: Angular. Length: About 4 to 5 mm. Width: About 3 mm. Color: Yellow-green, RHS 144A.

Seeds/fruit: None observed.

Disease/pest resistance: No test for disease/pest resistance have been performed yet.

Disease/pest susceptibility: No test for disease/pest resistance have been performed yet.

Temperature tolerance: Tolerant to a low temperature of about 2° C. and to a high temperature about 40° C.

I claim:

1. A new and distinct *Schlumbergera* plant named 'THOR-LIVIA', as illustrated and described herein.

* * * * *